United States Patent [19]

Tamm et al.

[11] Patent Number: 5,194,914
[45] Date of Patent: Mar. 16, 1993

[54] FURNACE FOR THE ELECTROTHERMAL ATOMIZATION OF SAMPLES IN ATOMIC ABSORPTION SPECTROSCOPY

[75] Inventors: Rolf Tamm, Salem; Gunther Rodel, Owingen, both of Fed. Rep. of Germany

[73] Assignee: Bodenseewerk Perkin-Elmer GmbH, Uberlingen, Fed. Rep. of Germany

[21] Appl. No.: 475,585

[22] Filed: Feb. 6, 1990

[30] Foreign Application Priority Data

Feb. 10, 1989 [DE] Fed. Rep. of Germany ... 8901529[U]

[51] Int. Cl.$^5$ ............................................. G01N 21/74
[52] U.S. Cl. ..................................... 356/312; 356/244
[58] Field of Search ............................ 356/312, 244

[56] References Cited

U.S. PATENT DOCUMENTS

| 4,111,563 | 9/1978 | Tamm ........................... 356/312 |
| 4,834,536 | 5/1989 | Tamm et al. ................... 356/312 |
| 4,953,977 | 9/1990 | Tamm ........................... 356/312 |

FOREIGN PATENT DOCUMENTS

| 2323774 | 11/1974 | Fed. Rep. of Germany . |
| 2554950 | 6/1977 | Fed. Rep. of Germany . |
| 3534417 | 4/1987 | Fed. Rep. of Germany . |
| 3545635 | 6/1987 | Fed. Rep. of Germany . |
| 3713503 | 2/1988 | Fed. Rep. of Germany . |
| 3722379 | 3/1988 | Fed. Rep. of Germany . |
| 3720376 | 12/1988 | Fed. Rep. of Germany . |

*Primary Examiner*—F. I. Evans
*Attorney, Agent, or Firm*—Edwin T. Grimes

[57] ABSTRACT

A tubular furnace having an inner body connecting by an integral radially extending web. The web is positioned on the side of the tubular furnace so that a sample placed in the inner body and resting in the bottom thereof will not be heated by the web. Other embodiments illustrate the web positioned at different axial locations.

11 Claims, 4 Drawing Sheets

FURNACE FOR THE ELECTROTHERMAL ATOMIZATION OF SAMPLES IN ATOMIC ABSORPTION SPECTROSCOPY

FIELD OF THE INVENTION

The invention relates generally to a furnace used to atomize samples in atomic absorption spectroscopy and more particularly to a furnace structure preventing the undesirable direct heating of the sample.

BACKGROUND OF THE INVENTION

Atomic absorption spectrometers serve to determine the amount or concentration of an element looked for in a sample. For this purpose a measuring light beam from a line-emitting light source, a hollow cathode lamp, for example, is directed to a photo-electrical detector. An atomizing device is arranged in the path of rays of this measuring light beam. The sample which is to be analyzed is atomized in this atomizing device such that the components of the sample are present in an atomic state. The measuring light beam contains the resonant lines of the element looked for. These resonant lines of the measuring light beam are absorbed by the atoms of the element looked for in the cloud of atoms, while, ideally, the other element contained in the sample do not influence the measuring light beam. Therefore, the measuring light beam is subjected to an attenuation, which is a measure of the number of the atoms looked for that are in the path of the measuring light beam. Thus, a measure of the concentration or the amount of the looked for element in the sample is obtained depending on the method of atomization applied.

For highly sensitive measurements electrothermal atomization is preferably used. In this method the sample is introduced into a furnace which is heated to a high temperature by passing electrical current therethrough. Thereby, the sample is dried, ashed and then atomized. Then a "cloud of atoms" is generated within the furnace in which cloud the atom looked for is present in an atomic state. The measuring light beam is passed through this cloud in the furnace.

Tubular furnaces for the electrothermal atomization of samples for atomic absorption spectroscope are known as "graphite tube atomizers". These furnaces consist of a small tube made of graphite which is held between two annular contacts. A high electrical current is passed through the contacts through the tube in its longitudinal direction. Thereby, the tube can be heated to high temperatures. The sample is inserted into the tube through a lateral inlet port and is atomzied when the tube is heated. The measuring light beam passes through the annular contacts and the bore of the tube in its longitudinal direction. The graphite tube is surrounded both inside and outside by an inert gas which prevents the tube from coming into contact with air or oxygen. Such graphite tube atomizers are illustrated and described in German patent application 23 14 207 and German patent application 21 48 783, which corresponds to U.S. Pat. No. 4,098,554 issued Jul. 4, 1978 and U.S. Pat. No. 3,778,156 issued Dec. 11, 1973, respectively.

From German patent application 25 54 950 which corresponds to U.S. Pat. No. 4,111,563 issued Sep. 5, 1978, a furnace for electrothermal atomization of liquid samples (graphite tube) is known, in which a tubular inner body is provided in the interior of the actual tubular furnace body. The inner body is arranged concentrically in the furnace body and extends only through the central area of the furnace body. In its center the furnace body is provided with a lateral inlet port. An inlet port aligned therewith is arranged in the tubular inner body. The inner body is connected to the furnace body through longitudinally extending webs, which extend in the longitudinal plane perpendicular to the inlet port.

This design of the furnace prevents disturbances which are caused by the inserted liquid spreading over large areas of the inner wall of the graphite tube and thus reaching relatively cool end portions of the tubular furnace. At the end portions, only incomplete vaporization is effected such that sample material is retained which disturbs subsequent measurements of other samples. Also, sample losses are avoided which can occur by the seeping of sample liquid into the porous graphite.

It is desirable to delay the atomization of the sample relative to the heating of the wall of the furnace. This is to ensure that the components of the sample, when they are atomized, do not precipitate onto relatively cool wall portions and that the sample is atomized as abruptly as possible. This provides a strong absorption signal to occur. From L'vov's publication in "Spectrochimica Acta" vol. 33B, 153-193, a platform, having a generally rectangular shape, made of pyrolytic graphite is known which is inserted into a furnace designed as a graphite tube. In order to reduce the contact with the graphite tube, wall grooves are provided along the longitudinal edge of the platform. In this way the sample is heated mostly indirectly by radiation of the inner wall of the furnace.

German patent application 29 24 123 which corresponds to U.S. Pat. No. 4,303,339 issued Dec. 1, 1981 shows a tubular furnace body (graphite tube) with a platform which is provided with a recess for accommodating the sample and is guided into the furnace body only along two opposite longitudinal edges.

The amount of sample which can be accommodated by this platform is limited. Furthermore, for the user the problem arises in that into a small furnace body an even smaller platform has to be inserted. This is a very complicated manipulation. Part of the electrical current flowing through the furnace body in its longitudinal direction also flows through the platform. Therefore, the platform is not only heated indirectly by radiation, but Joul's heat is generated within the platform itself.

From German patent application P 37 43 286, not pre-published, which corresponds to U.S. patent application No. 285,884 filed Dec. 16, 1988, it is known to arrange a hollow, generally semicylindrical inner body which is connected to the outer furnace body by a web, in a tubular furnace body. In this way the hollow, generally semicylindrical inner body is made integral with the tubular furnace body such that problems of handling are omitted. The inserted sample "faces" the wall of the outer furnace body, that is, it is indirectly heated by the radiation of this wall.

In this furnace a web is arranged symmetrically to the longitudinal center plane of the inner body and in the center of the inner body. However, the sample which is to be atomzied is dosed in this inner body center. Since the furnace is naturally arranged such that the hollow, generally semicylindrical inner body as "platform" extends substantially horizontally, i.e., the longitudinal center plane of the inner body extends vertically, the dosed sample accumulates in the area of the longitudinal center plane at the lowest point of the inner body. Thus, the dosed sample is located directly above the web. The unavoidable heat supplied by heat conduction through the web is exactly at the location where the sample which is to be atomized is located. This counteracts the desired heating of the sample with a delay relative to the heating of the outer furnace body.

SUMMARY OF THE INVENTION

The present invention is directed to a furnace having an inner body that delays the heating of a sample relative to the heating of an outer furnace body. This is accomplished by an inner body that is integral with the outer furnace body through a web that is narrow in its axial direction and arranged non-symmetrically on the inner body.

In this way the web is not located at the location of the dosed sample whereby the heating of the sample by heat conduction is counteracted. On the other hand, the inner body is a platform open to the inner wall of the furnace body. Therefore, the sample "faces" the inner wall of the furnace body and is thereby heated through radiation as soon as the furnace body has reached the required temperature. The inner body forms an integral component of the furnace such that problems of handling do not occur.

Accordingly, it is an objective of the present invention to delay the atomization of the sample relative to the heating up of the outer furnace body and to counteract the direct heating up of the sample by heat conduction.

Other objectives will become more readily apparent in view of the following more detained description.

DETAILED DESCRIPTION OF THE PREFERRED EMBODIMENT

Figure 1:
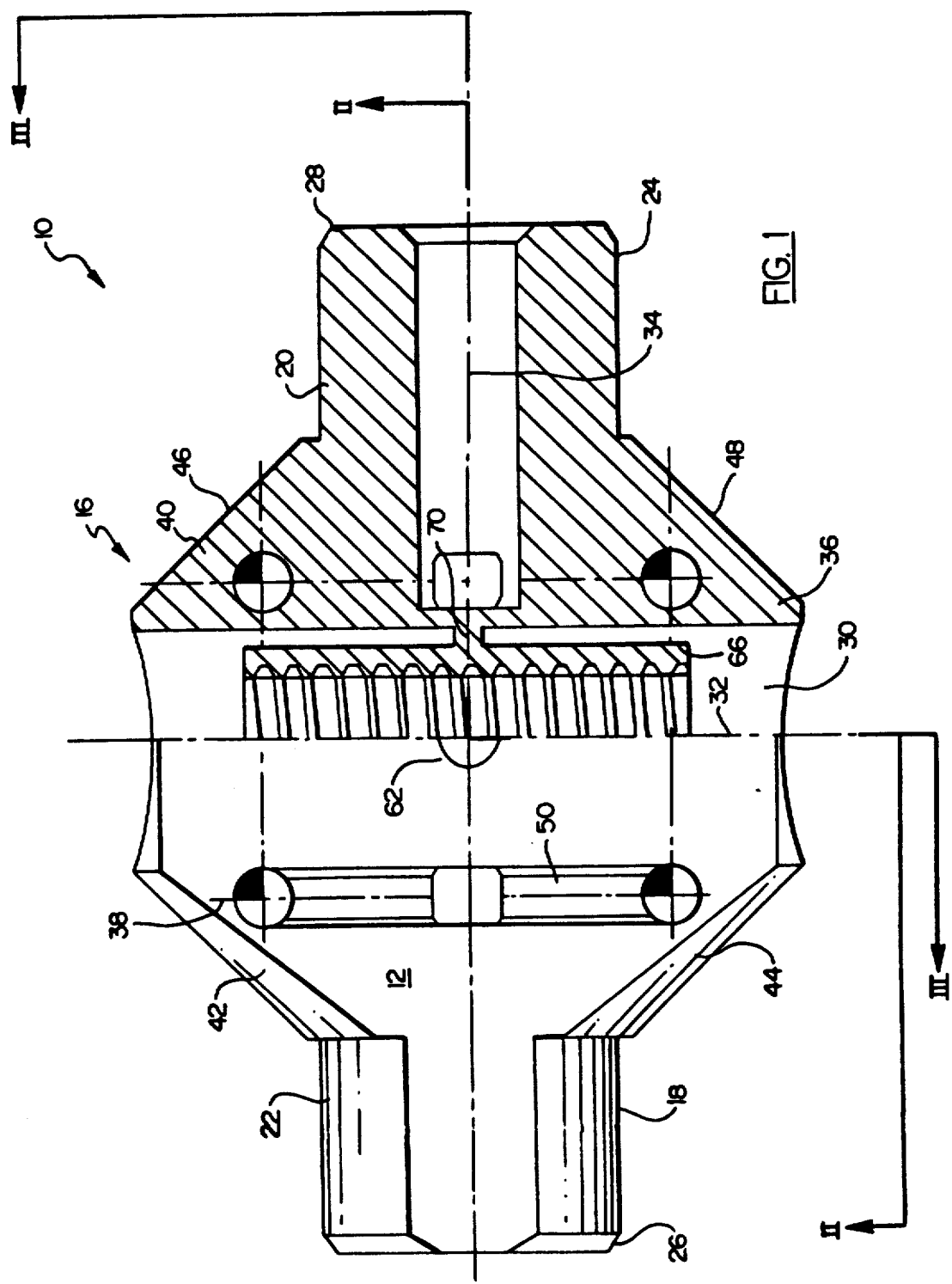
FIG. 1 shows a partially sectional plan view of a furnace with a hollow, generally semicylindrical platform being integral therewith and current supply transverse to the axis of the furnace body.
Figure 2:
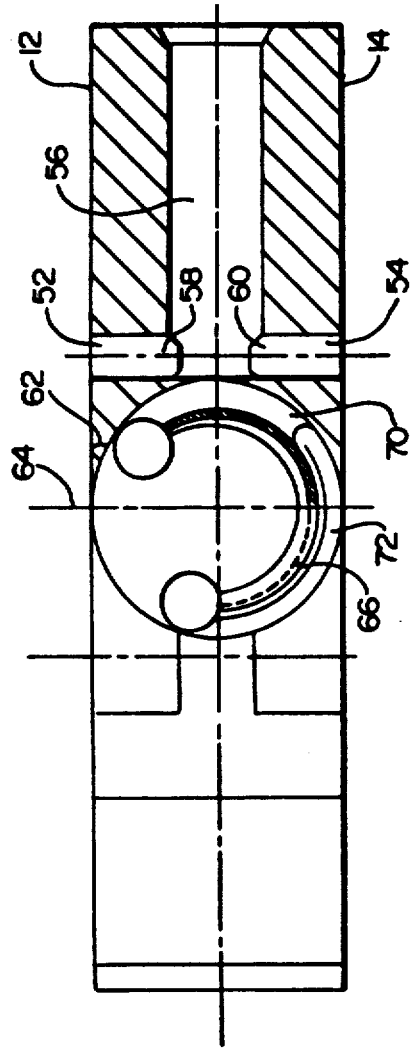
FIG. 2 shows a partially sectional lateral view of the furnace taken along the line II—II of FIG. 1.
Figure 3:
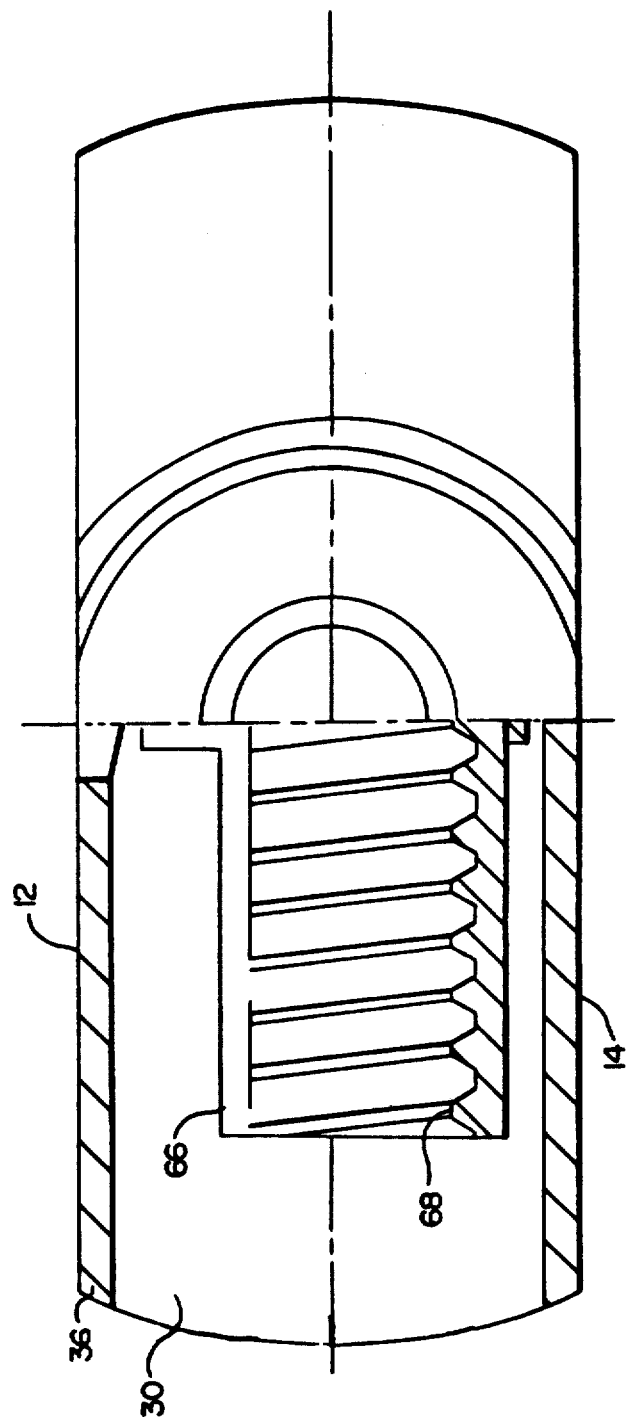
FIG. 3 shows a partially sectional end view of the furnace taken along the line III—III of FIG. 1.

In the furnace of FIGS. 1 to 3 numeral 10 designates a graphite piece which generally has the shape of a plate with an upper planar surface 12 and a lower planar surface 14. The graphite piece 10 has a center portion 16 which, in plan view, has substantially the shape of a regular octagon. Projections are provided on two diametrically opposite sides of the octagon and form contact pieces 18 and 20. These contact pieces 18 and 20 have cylindrical peripheral surfaces 22 and 24, respectively, but are limited by planar surfaces 12 and 14 respectively, at the bottom and at the top and are flattened thereby. The contact pieces 18 and 20 are provided with conical contact surfaces 26 and 28, respectively. The furnace is held by these contact surfaces 26 and 28 between contacts of the furnace through which power is supplied.

The sides of the octagon perpendicular to the sides with the contact pieces 18, 20 are connected by a bore 30. The axis 32 of the bore 30 extends perpendicular to the axis 34 of the contact pieces 18 and 20. The bore 30 forms the tubular furnace. The part of the center portion 16 between the sides connected by the bore 30 forms a furnace body 36.

Contact ribs 38 and 40 are integral with the furnace body 36 on both sides. The contact ribs 38 and 40 are trapezoidal in plan view of FIG. 1. The contact ribs 38 and 40 are limited at their top and at their bottom by planar surfaces 12 and 14 and on their sides by inclined side faces 42, 44 and 46, 48, respectively. The long parallel side of each trapezoid is adjacent to the furnace body 36. The short parallel side of each trapezoid is the side of the octagon mentioned first and carries the contact pieces 18 and 20, respectively. The contact ribs 38 and 40 have areas of reduced cross-section.

In the furnace, according to FIGS. 1 and 3, the reduction of the cross-section for the current supply along the central area of the furnace body 36 is achieved by grooves 50, 52 and 54, respectively, in the planar surfaces 12 and 14. The grooves extend parallel to the axis 32 of the furnace body 36 and end at a distance from the side faces 42, 44, and 46, 48, respectively. As can be seen from FIG. 2, the grooves, e.g., 52 and 54, are intersected by inert gas passages, e.g., 56. Therefore, the inert gas supplied through the inert gas passages passes through apertures 58 and 60 into the grooves 52 and 54 and emerges through these grooves on both sides and along the entire furnace body 36.

A particularly uniform temperature distribution is achieved by the reduction of the cross-section for the current supply in the central area of the furnace body 36.

The furnace body 36 has an inlet port 62 through which a sample which is to be analyze can be introduced into the furnace. The axis 64 of the inlet port 62 is perpendicular to the axes 32 and 34 of the furnace body 36 and of the contact pieces 18, 220. The axis 64 of the inlet port 62 together with the axis 32 of the furnace body 36 defines a longitudinal center plane. This is a plane perpendicular to the paper plane in FIG. 1 along the axis 32.

An inner body 66, which can be best observed in FIG. 3, is located in the bore 30 of the furnace body 36. The inner body 66 is of a hollow, generally semicylindrical shape and thus has approximately the shape of one half of a hollow cylinder. In the embodiment of FIG. 3 the inner surface of the inner body 66 has helical projections 68. In effect, these projections 68 form half of an internal thread. These projections 68 impede the divergence of a liquid sample introduced through the inlet port 62 in the longitudinal direction of the inner body 66. Making the projections 68 as a part of an internal thread is due to manufacturing reasons. First, the tubular furnace body can be threaded by a threading mechanism and the threading mechanism can be unscrewed, subsequently, one half of the inner body is bored out by two longitudinal bores, as illustrated in FIG. 3. The inner body is held in, in the middle of the furnace body 36 only by one single web 70.

In the embodiment according to FIGS. 1 and 3 this web 70 is arranged in the central area of the inner body 66, in the plane defined by the axes 34 and 64, for instance. An arcuated groove 72 is cut out of this web originally extending around the entire inner body between the inner body 66 and furnace body 36, such that the remaining web 70 extends through an angle about the axis 32 of the furnace which angle is clearly smaller than 180°. This remaining web 70 is arranged laterally or radially on the inner body, symmetrically to the axis 34 of the contact projections 18, 20. Hereby, two different objects are achieved.

First, current flow through the inner body 66 is prevented since the inner body does not form any bridge between the contact projections 18 and 20 through which the current could flow. Also, the web 70 does not form any such bridge so that no Joul's heat is generated within the web.

Second, the web 70 is not locate where the sample liquid accumulates during operation. During operation the furnace is situated as illustrated in FIG. 2. The inlet port 62 is located on top and the platform formed by the inner body 66. The platform is arranged substantially horizontal, such that the inserted sample liquid accumulates at the bottom of the hollow, generally semicylindrical platform. The web 70 is displaced from this location such that there is no direct heat conductive contact between the sample and the furnace body 36.

In operation, the furnace describe is fixed between two contacts by means of the contact projections 18 and 20 in an atomic absorption spectrometer. The measuring light beam of the atomic absorption spectrometer passes along the axis 32 of the furnace through the tubular furnace body 36, the light beam extending above the inner body 66. A sample is supplied to the inner body 66 through the inlet port 62. The furnace is heated to high temperature by passing electrical current through the furnace. The inner portion 66 is heated mostly indirectly by radiation. Thereby the sample is atomized. A cloud of atoms is produced in which the elements, and also an element looked for, are present in an atomic state. The amount of the looked for element can be determined from the absorption of the measuring light beam originating from a line emitting light source. The contacts on the side of the instrument surround the furnace to a large extent. Inert gas is supplied through the contacts such that no oxygen can get to the furnace, and the furnace being made of graphite does not burn at high temperatures The grooves and bores described distribute this inert gas such that the furnace is surrounded entirely by the inert gas. The current is supplied transversely to the direction of the measuring light beam and to the axis of the furnace. An optimally uniform temperature distribution along the furnace is achieved by the design described.

Figure 4:
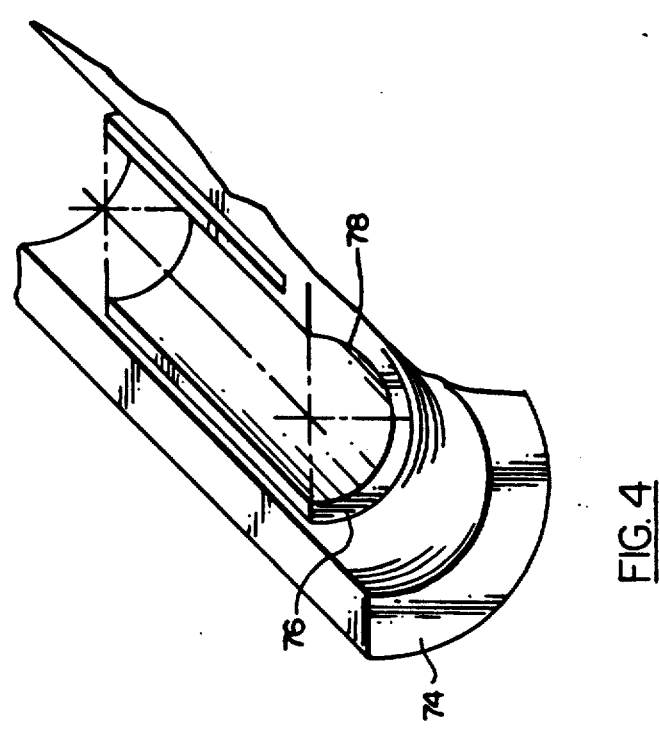
FIG. 4 is a schematic perspective illustration of a further embodiment of a furnace with a hollow, generally semicylindrical platform which is integral therewith and is held non-symmetrically.

FIG. 4 is a schematical perspective illustration of another embodiment of a furnace with an inner body 76. In the illustration of FIG. 4 the upper portion of the actual furnace body 74 is cut off in order to expose the inner body 76 and its holding at the outer furnace body 74. Here, the furnace body 74 is a graphite tube which is axially fixed between annular contact in a known manner and through which current flows in its longitudinal direction.

In the embodiment according to FIG. 4 the inner body 76 also forms a hollow, generally semicylindrical platform. The inner body 76 is connected to the furnace body 74 by means of a single web 78. However, in this arrangement this web 78 is not only arranged laterally, i.e., not at the bottom of the hollow, generally semicylindrical platform, but is provided also on one end of the inner body 76, i.e., axially displaced against the center of the inner body. Thereby, the web 78 is spaced even farther from the sample supplied to the central portion of the platform Thereby, the distance for the heat conduction from the furnace body 74 to the sample is further increased.

The arrangement of the web at the end of the inner body has the additional advantage that the web is also arranged outside of the central area of the furnace body 74, which is heated first and with the highest intensity and would accordingly cause the highest heat conduction to the inner body.

Figure 5:
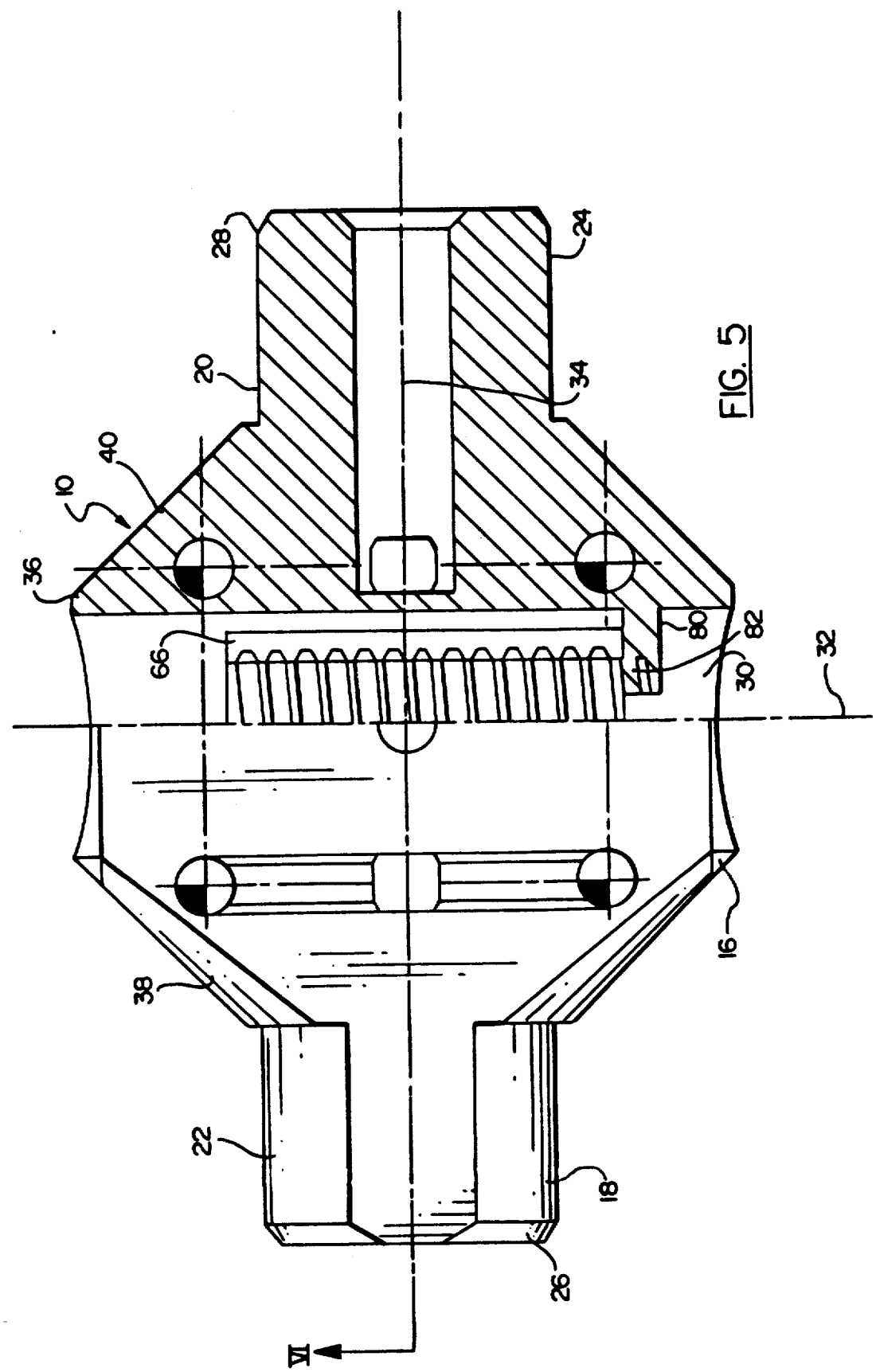
FIG. 5 shows a partially sectional plan view of a furnace similar to that of FIG. 1, wherein the platform is held at one end above a web in the furnace body.
Figure 6:
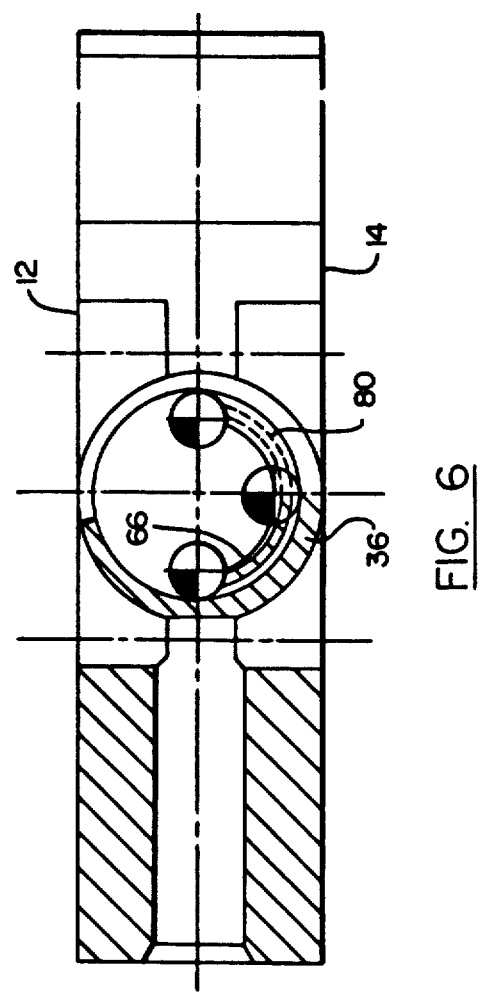
FIG. 6 shows a partially sectional end view of the furnace taken along the line VI—VI of FIG. 5.

FIGS. 5 and 6 show a transversely heated furnace which is constructed similarly to the furnace of FIGS. 1 and 3. Corresponding elements in FIGS. 5 and 6 are designated by the same numerals as in FIGS. 1 to 3.

In the embodiment according to FIGS. 5 and 6 the web 80, which connects the inner body 66 with the furnace body 36, is provided laterally and at one end of the inner body 66. This is similar to the longitudinally heated furnace of FIG. 4. However, in the embodiment of FIGS. 5 and 6 the web is additionally located on an axial projection 82 which is formed on the end face of the inner body 66.

What is claimed is:

1. A furnace for the electrothermal atomization of samples in atomic absorption spectroscopy comprising:
   a tubular, electrically conductive furnace body having a lateral inlet port;
   an inner body formed from a portion of a tube having an opening facing the inlet port, said inner body positioned within and integral with said furnace body; and
   a single web holding said inner body within said furnace spaced from the wall of said furnace body, said web extending in a direction substantially perpendicular to the longitudinal axis of said inner body, being narrow in its axial direction and arranged non-symmetrically on said inner body such that the axis of the inlet port does not extend therethrough.

2. A furnace as set forth in claim 1, wherein:
   said inner body has a hollow, generally semicylindrical shape.

3. A furnace as set forth in claim 1 wherein:
   said web is provided on only one side of the longitudinal center plane of the inner body.

4. A furnace as set forth in claim 1 further comprising:
   lateral contact elements on opposite sides of said tubular furnace body through which the furnace can be held between contacts on the side of an instrument and through which current can be passed through said furnace body in a circumferential direction.

5. A furnace for the electrothermal atomization of samples in atomic absorption spectroscopy comprising:
   a tubular, electrically conductive furnace body having a lateral inlet port;
   an inner body formed from a portion of a tube having an opening facing the inlet port, said inner body positioned within and integral with said furnace body; and
   a web holding said inner body within said furnace spaced from the wall of said furnace body, said web extending in a direction substantially perpendicular to the longitudinal axis of said inner body, being narrow in its axial direction and arranged non-symmetrically on said inner body, said web being axially displaced relative to the center of said inner body, such that the axis of the inlet port does not extend therethrough.

6. A furnace as set forth in claim 5 wherein:
said web is provided at one end of the inner body.

7. A furnace as set forth in claim 6 wherein:
said web is provided at an axial projection of the inner body formed on one side of the longitudinal center plane of the inner body.

8. A graphite furnace for the electrothermal atomization of samples in atomic absorption spectroscopy comprising:
a tubular electrically conductive furnace body having an inlet port therein;
a partial tubular inner body concentrically positioned entirely within said furnace body; and
a single web holding said inner body within said furnace body, said web extending in a direction substantially perpendicular to the longitudinal axis of said inner body and radially from said furnace body and integrally attached to said inner body at a location away from the bottom of said inner body where a fluid sample is placed before atomization.

9. A graphite furnace as in claim 8 wherein:
said location is at the axial center of said inner body.

10. A graphite furnace as in claim 8 further comprising:
an axial projection extending from said inner body, and said location is on said axial projection.

11. A graphite furnace for the electrothermal atomization of samples in atomic absorption spectroscopy comprising:
a tubular electrically conductive furnace body having an inlet port therein;
a partial tubular inner body concentrically positioned entirely within said furnace body; and
a web holding said inner body within said furnace body, said web extending in a direction substantially perpendicular to the longitudinal axis of said inner body and radially from said furnace body and integrally attached to said inner body at a location at one end of said inner body away from the bottom of said inner body where a fluid sample is placed before atomization.

* * * * *